: (12) United States Patent
Jiang et al.

(10) Patent No.: US 9,841,512 B2
(45) Date of Patent: Dec. 12, 2017

(54) SYSTEM AND METHOD FOR REDUCING RADIATION-INDUCED FALSE COUNTS IN AN INSPECTION SYSTEM (71) Applicant: KLA-Tencor Corporation, Milpitas, CA (US)

(72) Inventors: Ximan Jiang, San Mateo, CA (US); Anatoly Romanovsky, Palo Alto, CA (US); Christian Wolters, San Jose, CA (US); Stephen Biellak, Sunnyvale, CA (US); Mous Tatarkhanov, Castro Valley, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/946,563

(22) Filed: Nov. 19, 2015

(65) Prior Publication Data
US 2016/0334516 A1    Nov. 17, 2016

Related U.S. Application Data (60) Provisional application No. 62/161,454, filed on May 14, 2015.

(51) Int. Cl.
*G01T 1/24* (2006.01)
*G01N 21/95* (2006.01)

(52) U.S. Cl.
CPC .......... *G01T 1/24* (2013.01); *G01N 21/9501* (2013.01)

(58) Field of Classification Search
CPC .................................................. G01T 1/208
See application file for complete search history.

(56) References Cited

U.S. PATENT DOCUMENTS 2,535,066 A * 12/1950 Herzog ............... G01V 5/02
250/253
3,842,278 A * 10/1974 Noakes ............... G01T 1/204
250/367

(Continued)

FOREIGN PATENT DOCUMENTS

JP    2012177714 A    9/2012

OTHER PUBLICATIONS

SEMI Standards, M50-0310 Test Methods for Determining Capture Rate and False Count Rate for Surface Scanning Inspection Systems by the Overlay Method, Nov. 2009, 1 page, printed online at: <http://ams.semi.org/ebusiness/standards/SEMIStandardDetail.aspx?ProductID=211&DownloadID=1572>.

(Continued)

*Primary Examiner* — Edwin Gunberg
(74) *Attorney, Agent, or Firm* — Suiter Swantz pc llo (57) ABSTRACT An inspection system with radiation-induced false count mitigation includes an illumination source configured to illuminate a sample, a detector assembly comprising an illumination sensor configured to detect illumination from the sample, and one or more radiation sensors configured to detect particle radiation, and control circuitry communicatively coupled to the detector. The control circuitry is configured to perform the steps of determining a set of radiation detection events based on one or more radiation signals received from the radiation sensors, determining a set of imaging events based on the illumination signal received from the illumination sensor, comparing the set of radiation detection events to the set of imaging events to generate a set of coincidence events, wherein the set of coincidence events comprises simultaneous imaging and radiation detection events, and excluding the set of coinci- (Continued)

dence events from the set of imaging events to generate a set of identified defect sites.

32 Claims, 9 Drawing Sheets

(56) References Cited

U.S. PATENT DOCUMENTS

| | | | | |
|---|---|---|---|---|
| 4,740,708 | A | * | 4/1988 | Batchelder .............. G01N 21/94 250/559.16 |
| 8,084,741 | B2 | * | 12/2011 | Gagnon ................. A61B 6/037 250/362 |
| 2007/0133863 | A1 | | 6/2007 | Sakai et al. |
| 2011/0102771 | A1 | | 5/2011 | Shapirov |
| 2012/0044486 | A1 | | 2/2012 | Chen et al. |
| 2013/0264481 | A1 | | 10/2013 | Chern et al. |

OTHER PUBLICATIONS

Muons, The Cosmic Connection, 3 pages, Printed online Apr. 11, 2016 at: <http://cosmic.lbl.gov/SKliewer/Cosmic_Rays/Muons.htm>.

Don Groom, Cosmic Rays and Other Nonsense in Astronomical CCD Imagers, Experimental Astronomy, vol. 14, No. 1, pp. 45-55, 2002.

A.R. Smith et al., Radiation events in astronomical CCD images, Electronic Imaging 2002, International Society for Optics and Photonics, Published Jan. 23, 2002, 13 pages.

A.L. Mitchell et al., Skyshine contribution to gamma ray background between 0 and 4 MeV, Pacific Northwest Laboratory, Aug. 2009, 27 pages.

D.R. Nelson et al., Gamma-Ray Interactions with Matter, Passive Nondestructive Analysis of Nuclear Materials, Los Alamos National Laboratory, pp. 27-42, 1991.

PCT Search Report for International Application No. PCT/US2016/031843 dated Sep. 1, 2016, 3 pages.

\* cited by examiner

SYSTEM AND METHOD FOR REDUCING RADIATION-INDUCED FALSE COUNTS IN AN INSPECTION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled Radiation-Induced False Count Reduction in Inspection Systems, naming Ximan Jiang, Anatoly Romanovsky, Christian Wolters, and Stephen Biellak as inventors, filed May 14, 2015, Application Ser. No. 62/161,454, which is incorporated herein by reference in the entirety.

TECHNICAL FIELD

The present disclosure relates generally to the field of noise reduction in inspection systems, and, in particular, to the reduction of noise associated with particle radiation in wafer inspection systems.

BACKGROUND

False positives, or false counts, are undesirable in any inspection situation. False counts in an inspection system can arise from multiple sources. This may include electronic noise associated with detectors in the system as well as external noise associated with photons or radiative particles from sources other than the sample of interest. In the context of inspection systems, a false count occurs when a signal not associated with a sample is detected by one or more detectors and is incorrectly associated with properties of the sample. Radiation sources that may affect the false count rate of an inspection system may include, but are not limited to, the decay of trace levels of radioactive isotopes near the inspection system as well as high energy cosmic radiation by-products generated in the atmosphere. These radiation sources may produce radiative particles and/or photons including, but not limited to, alpha particles, beta particles, neutrons, muons, and gamma rays. For example, muons are primarily generated as a by-product of the interaction of cosmic radiation with the atmosphere. Radiative particles can also be generated through inelastic scattering from materials in close proximity to the inspection system.

Advances in the application of multi-pixel detectors in inspection systems have resulted in increased conversion gain and lower noise readout electronics. However, these advances have also resulted in increased sensitivity to the detection of particle radiation, such as muons, gamma particles, and alpha particles, to name a few. Therefore, it is desirable to provide a method and system that cures the defects identified above in previous approaches.

SUMMARY

An inspection system with radiation-induced false count mitigation is disclosed in accordance with one or more illustrative embodiments of the present disclosure. In one illustrative embodiment, the inspection system includes an illumination source configured to illuminate a sample. In another illustrative embodiment, the inspection system includes a detector assembly. In one illustrative embodiment, the detector assembly comprises an illumination sensor configured to detect illumination from the sample. In another illustrative embodiment, the detector assembly comprises one or more radiation sensors configured to detect particle radiation. In another illustrative embodiment, the inspection system includes one or more controllers communicatively coupled to the illumination sensor and the one or more radiation sensors. In one illustrative embodiment, the one or more controllers are configured to identify a set of illumination detection events based on an illumination signal received from the illumination sensor. In another illustrative embodiment, the one or more controllers are configured to identify a set of radiation detection events based on one or more radiation signals received from the one or more radiation sensors. In another illustrative embodiment, the one or more controllers are configured to compare the set of radiation detection events to the set of illumination detection events to identify a set of coincidence events. In this way, the set of coincidence events corresponds to simultaneous occurrences of radiation detection events and illumination detection events. In another illustrative embodiment, the one or more controllers are configured to exclude the set of coincidence events from the set of illumination detection events to generate a set of identified features on the sample.

An inspection system with radiation-induced false count mitigation is disclosed in accordance with one or more illustrative embodiments of the present disclosure. In one illustrative embodiment, the inspection system includes an illumination source configured to illuminate a sample. In another illustrative embodiment, the inspection system includes a detector assembly. In one illustrative embodiment, the detector assembly includes an illumination sensor configured to detect illumination from the sample. In another illustrative embodiment, the detector assembly includes one or more radiation sensors configured to detect particle radiation. In another illustrative embodiment, the inspection system includes one or more controllers communicatively coupled to the illumination sensor and the one or more radiation sensors. In one illustrative embodiment, the one or more controllers are configured to identify a set of radiation detection events based on one or more radiation signals received from the one or more radiation sensors. In another illustrative embodiment, the one or more controllers are configured to generate a set of radiation detection event timestamps associated with the set of radiation detection events. In another illustrative embodiment, the one or more controllers are configured to identify a set of illumination detection events based on the illumination signal received from the illumination sensor. In another illustrative embodiment, the one or more controllers are configured to generate a set of illumination detection event timestamps associated with the set of imaging events. In another illustrative embodiment, the one or more controllers are configured to compare the set of illumination detection event timestamps to the set of radiation detection event timestamps to generate a set of coincidence events. In this way, the set of coincidence events comprises illumination detection events and radiation detection events with matching timestamps. In another illustrative embodiment, the one or more controllers are configured to exclude the set of coincidence events from the set of detection events to generate a set of identified features on the sample A method for reducing radiation-induced false counts on a detector in an inspection system is disclosed in accordance with one illustrative embodiment of the present disclosure. In one illustrative embodiment, the method includes the step of illuminating at least a portion of a sample with a beam of illumination. In another illustrative embodiment, the method includes the step of identifying a set of radiation detection events based on one or more radiation signals received from one or more radiation sensors. In another illustrative embodiment, the method includes the step of generating a set of radiation detection event timestamps associated with the set of radiation detection events. In another illustrative embodiment, the method includes the step of identifying a set of illumination detection events based on the illumination signal received from an illumination sensor. In another illustrative embodiment, the method includes the step of generating a set of illumination detection event timestamps associated with the set of imaging events. In another illustrative embodiment, the method includes the step of comparing the set of illumination detection event timestamps to the set of radiation detection event timestamps to generate a set of coincidence events. In this way, the set of coincidence events comprises illumination detection events and radiation detection events with matching timestamps. In another illustrative embodiment, the method includes the step of excluding the set of coincidence events from the set of illumination detection events to generate a set of identified defect sites on the sample.

DETAILED DESCRIPTION

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 5, a system and method for reducing false counts in an inspection system are described in accordance with one or more embodiments of the disclosure. Embodiments of the present disclosure are directed to an inspection system with false count mitigation capabilities that reduce false counts generated by high energy particles (e.g., muons). Additional embodiments are directed to wafer inspection systems with false count mitigation capabilities that reduce false counts generated by additional radiation sources (e.g., alpha particles, beta particles, neutrons, muons, and gamma rays). For the purposes of the present disclosure, the terms "beam of radiation" and "radiation beam" are defined as radiative energy in the form of radiative particles and/or photons propagating along a defined path. Further, for the purposes of the present disclosure, the term "particle radiation" is defined to include radiation associated with sources other than the sample and includes, but is not limited to, alpha particles, beta particles, neutrons, muons, or gamma rays.

It is recognized herein that in the context of inspection systems, false counts may be generated by the detection of background radiation not associated with the sample of interest. It is further recognized that many semiconductor-based detectors configured for the detection of electromagnetic illumination such as ultraviolet (UV) or visible wavelengths are also sensitive to background radiation and that the degree of sensitivity is related to multiple factors including, but not limited to, the radiation flux, the detector design, and the operational conditions of the detector. By way of a non-limiting example, the sensitivity of a Charge Coupled Device (CCD) to radiation sources is in part a function of the charge-to-voltage conversion gain of the device, which describes the voltage induced by the generation of an electron in response to a detected event. In this way, increasing the conversion gain of a CCD increases the sensitivity of the device to any illumination detection event, which may include both the desired signal as well as background noise signals (e.g., radiation detection events).

In some applications, it is desirable to operate detectors at high sensitivity levels in order to maximize the resolution and sensitivity of the wafer inspection system to the illumination signal. By way of non-limiting example, detectors in unpatterned wafer inspection systems may be operated at high sensitivity levels in order to detect subtle differences between illumination signals associated with defect regions and non-defect regions. However, operating the detectors at high sensitivity correspondingly increases the impact of noise from radiative sources not associated with the sample that leads to false counts.

Figure 1:
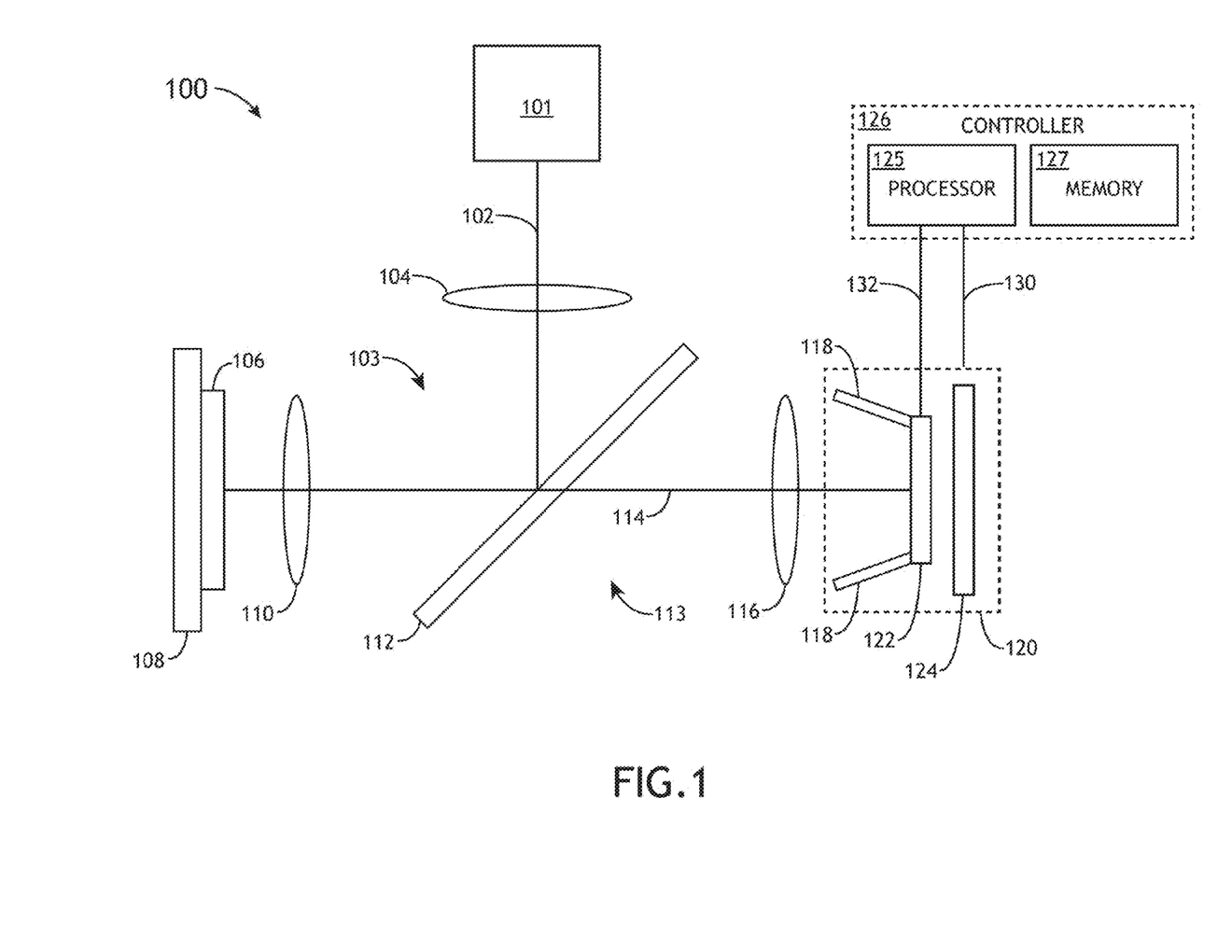
FIG. 1 is a schematic diagram illustrating an inspection system with radiation-induced false count mitigation, in accordance with one or more embodiments of the present disclosure.

FIGS. 1A and 1B illustrate an inspection system 100 with radiation-induced false count mitigation capabilities, in accordance with one or more embodiments of the present disclosure. In one embodiment, the system 100 includes an illumination source 101 configured to generate a beam of illumination 102. The illumination source 101 is configured to generate a beam of illumination 102 including a selected wavelength or a wavelength range such as, but not limited to, ultraviolet (UV), extreme ultraviolet (EUV), deep ultraviolet (DUV), vacuum ultraviolet light (VUV), visible, or infrared (IR) wavelengths of light. For example, the illumination source 101 may include any source capable of emitting illumination in the range of approximately 100 nm to 450 nm. For example, the illumination source 101 may include, but is not limited to, a narrow band source (e.g., laser source) or a broadband source (e.g., a Laser Sustained Plasma (LSP) source, a discharge lamp, or the like). By way of non-limiting example, the illumination source 101 may be a UV laser (e.g. an excimer laser or the like) with an output wavelength of 266 nm.

In one embodiment, the system 100 includes an illumination pathway 103 for directing at least a portion of the beam of illumination 102 to a sample 106. The illumination pathway 103 may include any number and type of optical elements suitable for delivering the beam of illumination 102 from the output of the illumination source 101 to the surface of the sample 106. For example, the illumination pathway 103 may include, but is not limited to, one or more lenses 104, one or more beamsplitters 112, one or more collimating elements (not shown), one or more filters (not shown), one or more polarizing elements (not shown) or one or more focusing elements 110 for directing, focusing, and otherwise processing illumination emitted by the illumination source 101.

In another embodiment, the system 100 includes a stage assembly 108 suitable for securing and positioning a sample 106. The stage assembly 108 may include any sample stage architecture known in the art. By way of a non-limiting example, the stage assembly 108 may include a linear stage. By way of another example, the stage assembly 108 may include a rotational stage. The sample 106 may include a wafer, such as, but not limited to, an unpatterned semiconductor wafer.

In one embodiment, the system 100 includes an imaging pathway 113 configured to direct illumination from the sample 106 to a detector assembly 120. In one embodiment, the imaging pathway 113 includes an objective lens 110. In another embodiment, the imaging pathway 113 includes a multi-lens imaging system. By way of non-limiting example, a multi-lens imaging system may include an objective lens 110 configured to collect imaging illumination 114 from the sample and one or more lenses 116 configured to generate an image of the sample on an detector assembly 120. In this way, an objective lens 110 may simultaneously focus an illumination beam 102 onto the sample and collect imaging illumination 114 from the sample. In one embodiment, a beam splitter 112 is positioned to overlap at least a portion of the illumination pathway 103 and the imaging pathway 113. It is noted herein that the beam splitter 112 is not intended to be limiting and need not be present in all embodiments of the present disclosure. In another embodiment, the illumination pathway 103 and the imaging pathway 113 are non-collinear and include independent optical elements.

In one embodiment, the detector assembly 120 includes one or more detectors communicatively coupled to one or more controllers 126. In one embodiment, a detector assembly 120 includes an illumination sensor 122 suitable for detecting imaging illumination 114 scattered or reflected from a sample 106. In another embodiment, the detector assembly 120 further includes one or more radiation sensors 124 suitable for detecting radiation (e.g., muons, alpha particles, beta particles, and/or gamma rays) from sources other than the sample 106. In this way, radiation detection events detected on the illumination sensor 122 may be simultaneously detected by one or more radiation sensors 124 and discarded as noise.

Figure 2A:
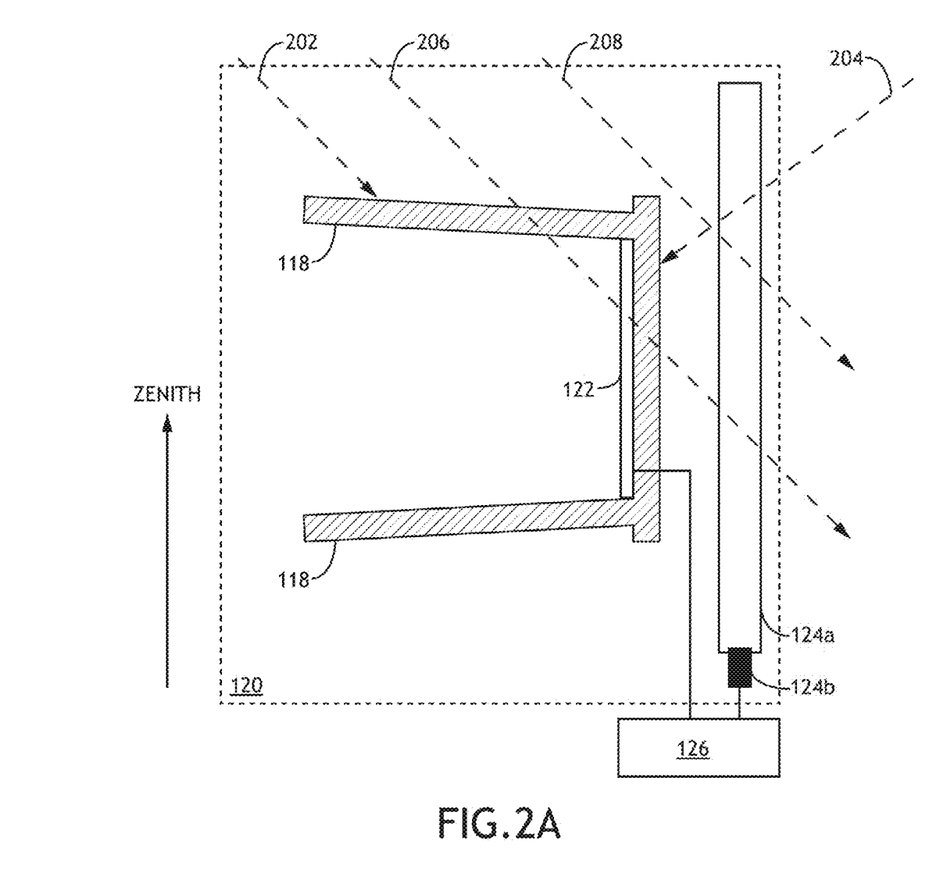
FIG. 2A is a schematic diagram illustrating beams of radiation incident on an illumination sensor and a radiation sensor, in accordance with one or more embodiments of the present disclosure.
Figure 2B:
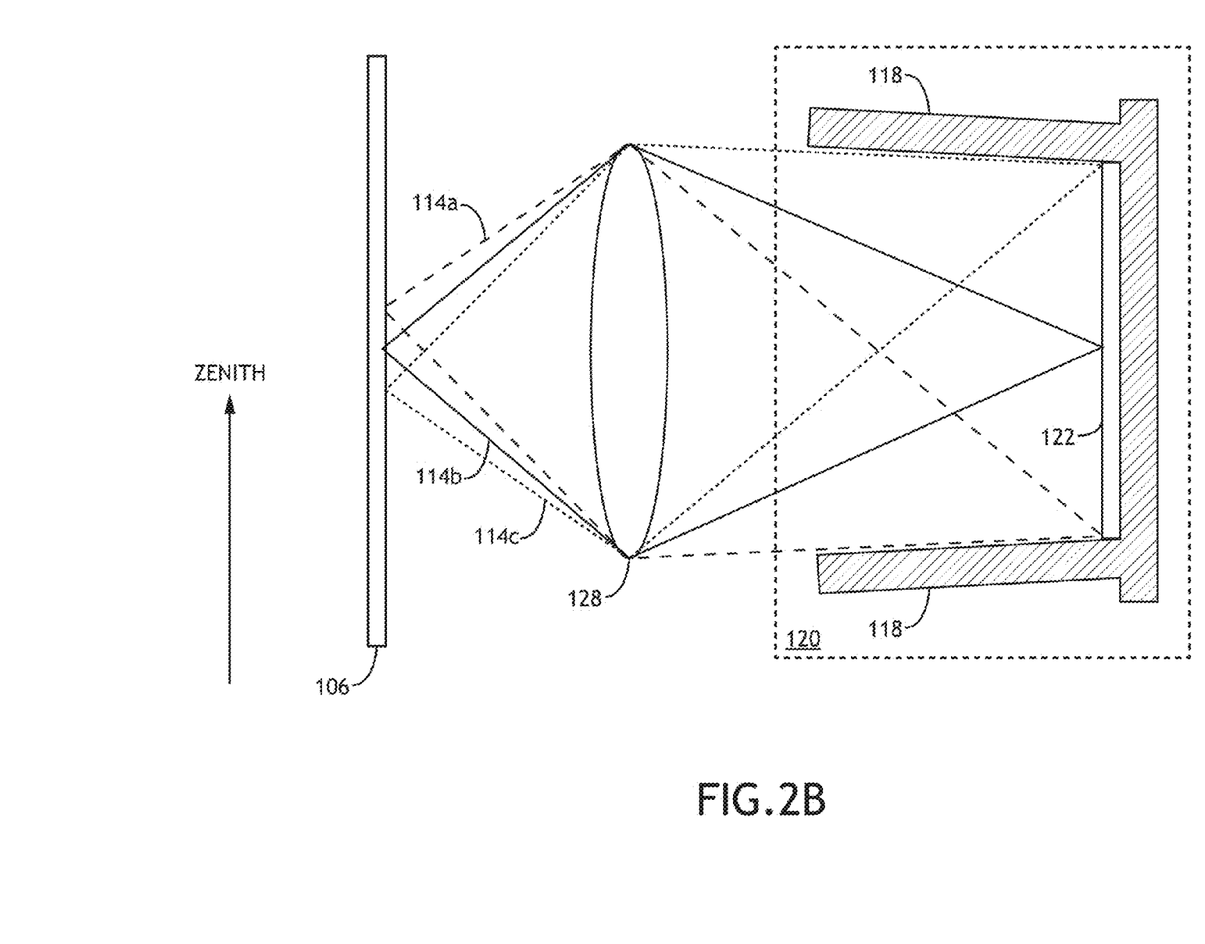
FIG. 2B is a schematic diagram illustrating the positioning of radiation shields to block radiation from solid angles not associated with imaging illumination from a sample, in accordance with one or more embodiments of the present disclosure.

FIGS. 2A and 2B illustrate a detector assembly 120 including an illumination sensor 122 and a proximate radiation sensor 124, in accordance with one or more embodiments of the present disclosure. In one embodiment, one or more radiation shields 118 are positioned around an illumination sensor 122 and are configured to absorb or redirect radiation (e.g. radiation beams 202 and 204) such that the radiation does not reach the sensor 122. The one or more radiation shields may be formed from any material known in the art suitable for preventing background radiation from reaching an illumination sensor 122. In one embodiment, the radiation shields 118 are formed from one or more heavy elements. For example, the radiation shields 118 may be, but are not required to be, formed from at least one of lead, tungsten, antimony, tin, or bismuth. It is noted herein that the thickness of the one or more radiation shields may be adjusted according to material properties to block radiation from reaching an illumination sensor 122. The one or more the radiation shields 118 may be further configured as structural or functional components in a detector assembly 120. For example, the one or more radiation shields 118 may be configured to stabilize or position an illumination sensor 122. In another embodiment, the one or more radiation shields 118 are integrated into a mounting package (e.g. a ceramic mounting package) attaching an illumination sensor 122 to additional components of the system 100. In another embodiment, the radiation shields 118 are further configured to operate as a heat sink for the illumination sensor 122.

In one embodiment, one or more radiation shields 118 are positioned to block radiation from all solid angles not associated with imaging illumination 114. Referring now to FIG. 2B, in one embodiment, one or more imaging lenses 128 generate an image of the sample 106 on the illumination sensor 122. Imaging rays 114a, 114b, and 114c represent imaging illumination from the entire field of view of the imaging system; specifically rays 114a and 114c represent rays covering the solid angle of the illumination sensor 122 associated with imaging illumination 114. In one embodiment, one or more radiation shields 118 are positioned in a rotationally symmetric configuration around the illumination sensor 122. For example, a beam of radiation 202 is blocked by this configuration. In another embodiment, one or more radiation shields are positioned behind the illumination sensor 122 in order to block beams of radiation (e.g. beam of radiation 204) incident from an end of the illumination sensor 122 opposite the sample 106.

It is noted herein that some sources of radiation may interact with the illumination sensor 122 despite the presence of radiation shields 118. By way of non-limiting example, beams of radiation with paths within the solid angle associated with imaging illumination 114 may interact with the illumination sensor 122. By way of a second non-limiting example, high energy radiation sources including, but not limited to, muons or gamma rays may propagate through one or more radiation shields 118 and may interact with the illumination sensor 122. In one embodiment, one or more radiation sensors 124 are positioned proximate to the illumination sensor 122 to detect beams of radiation that interact with the illumination sensor 122 (e.g. beam of radiation 206).

It is noted herein that a radiation sensor 124 may include one or more of any sensor type known in the art configured to detect particle radiation and may include, but is not limited to, a scintillation sensor, a semiconductor device, or a dosimeter. It is further noted that an illumination sensor 122 may include one or more of any sensor type known in the art configured to detect illumination. By way of non-limiting example, an illumination sensor 122 may include multiple pixel sensors including, but not limited to CCD devices, complementary metal-oxide semiconductor (CMOS) devices, and the like. By way of a second non-limiting example, an illumination sensor 122 may include single pixel sensors including, but not limited to, photomultiplier tube (PMT) sensors, photodiodes, or avalanche photodiode (APD) sensors.

In one embodiment, a radiation sensor 124 is configured as a scintillation sensor including a scintillating material 124a coupled to a photomultiplier tube (PMT) 124b. In this way, the PMT 124b detects one or more photons emitted by the scintillating material 124a in response to the detection of one or more radiation detection events. In another embodiment, the scintillating material 124a is configured as a waveguide such that at least a portion of the photons emitted by the scintillating material 124a are guided to the PMT 124b through total internal reflection.

It is contemplated herein that the relative timing between an illumination detection event of an illumination sensor 122 and a radiation detection event of a proximate radiation sensor 124 may be used to determine the presence of a radiation-induced false count. In one embodiment, one or more radiation sensors 124 are positioned proximate to an illumination sensor 122 and are further positioned such that illumination from the sample 106 is blocked. A beam of radiation 206 that interacts with both an illumination sensor 122 and a proximate radiation sensor 124 may trigger an event on both sensors; since illumination from the sample does not reach the radiation sensor, such an event may be identified as a false count. Similarly, detection events on the illumination sensor 122 not associated with a corresponding radiation detection event on the one or more radiation sensors 124 may be identified as valid. Furthermore, a beam of radiation 208 that interacts with the radiation sensor 124 but not the illumination sensor 122 may be disregarded. However, a beam of radiation 208 may be incident on a radiation sensor 124 at the same time as an illumination event associated with illumination from the sample is incident on an illumination sensor 122. In this way, a valid signal will be interpreted as invalid; such an event may be referred to as a false coincidence event. It is noted herein that the rate of false coincidence events may be, but is not limited to be, dependent on the size of the one or more radiation sensors 124 or the positions of one or more radiation sensors 124 relative to an illumination sensor 122.

In one embodiment, one or more radiation sensors 124 are positioned relative to an illumination sensor 122 to cover all solid angles through which beams of radiation are incident on the illumination sensor 122. In this way, false counts associated with a beam of radiation incident on and detected by an illumination sensor 122 may be mitigated. It is noted herein that the relative size and position of one or more radiation sensors 124 proximate to an illumination sensor 122 will determine the degree to which beams of radiation passing through an illumination sensor 122 may be detected by the one or more radiation sensors 124. If the solid angle is greater to or equal to $2\pi$ defining a hemisphere for all points on the illumination sensor 122, then beams of radiation from any angle incident on the illumination sensor 122 may be detected by the one or more radiation sensors 124.

The solid angle of the one or more radiation sensors 124 measured from a point on the illumination sensor 122 may be increased by increasing the size of the active area of one or more radiation sensors 124 relative to the active area of the illumination sensor 122. Additional methods to increase the solid angle of the one or more radiation sensors 124 measured from a point on the illumination sensor include, but are not limited to, increasing the number of sensors and decreasing the distance between an illumination sensor 122 and one or more radiation sensors 124.

It is further noted that the radiation flux of high energy radiation associated with by-products of cosmic rays (e.g. muons) is not uniform and is maximum near the zenith. The incidence of high energy radiation associated with by-products of cosmic rays may thus be minimized by minimizing the cross-sectional area of an illumination sensor 122 in the plane normal to the zenith. It is further noted that minimizing the pixel dimensions of the illumination sensor 122 may further reduce the incidence of such high energy radiation and thus the false count rate. However, the sensor pixel volume also influences device performance characteristics such as the resolution, mean transfer function, full-well potential, dynamic range, speed, and cost; therefore, the minimization of pixel volume to reduce the false count rate may be balanced against these factors.

Figure 3A:
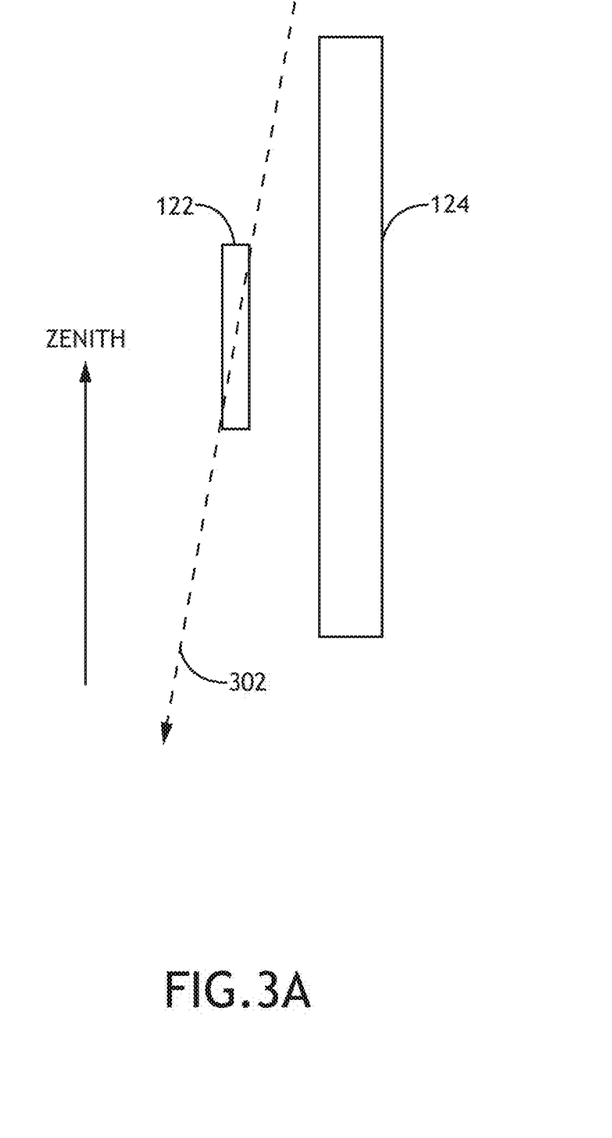
FIG. 3A is a schematic diagram illustrating the positioning of a single radiation sensor proximate to a vertical illumination sensor, in accordance with one or more embodiments of the present disclosure.
Figure 3B:
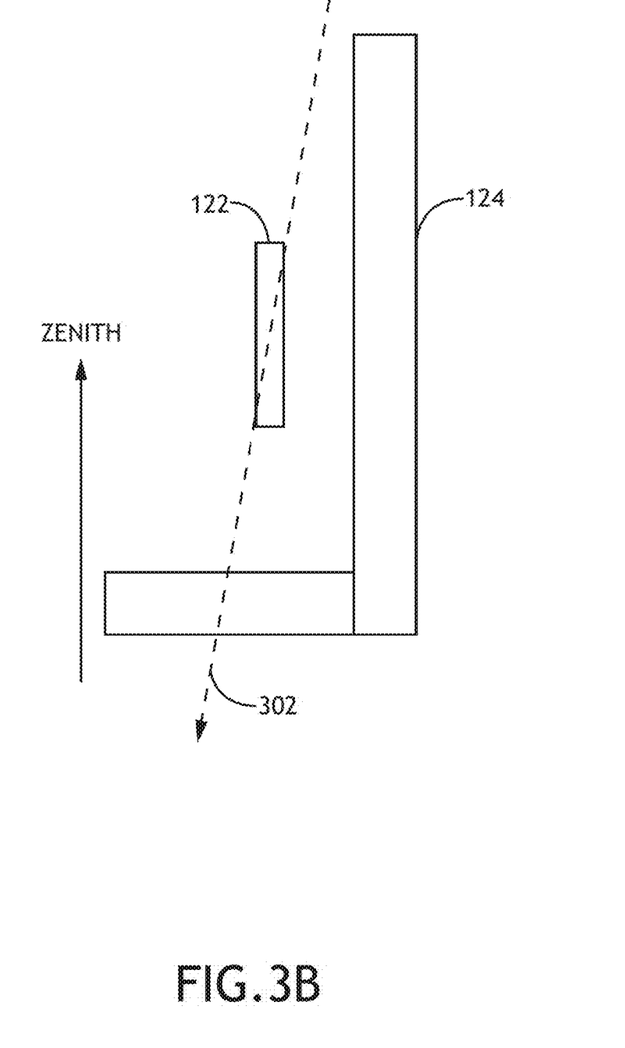
FIG. 3B is a schematic diagram illustrating the positioning of a two radiation sensors proximate to a vertical illumination sensor in order to capture all beam radiation paths passing through the illumination sensor, in accordance with one or more embodiments of the present disclosure.
Figure 3C:
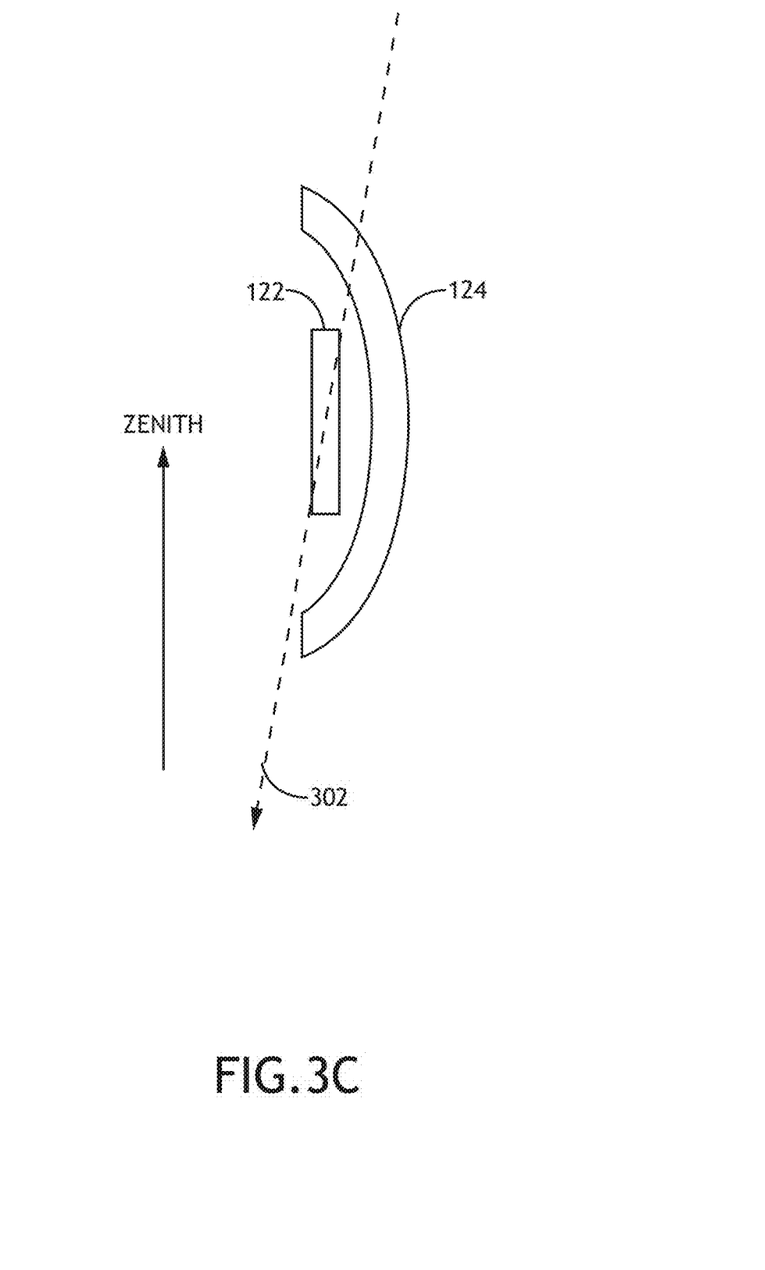
FIG. 3C is a schematic diagram illustrating the positioning of a single curved radiation sensor proximate to a vertical illumination sensor in order to capture all beam radiation paths passing through the illumination sensor, in accordance with one or more embodiments of the present disclosure.
Figure 3D:
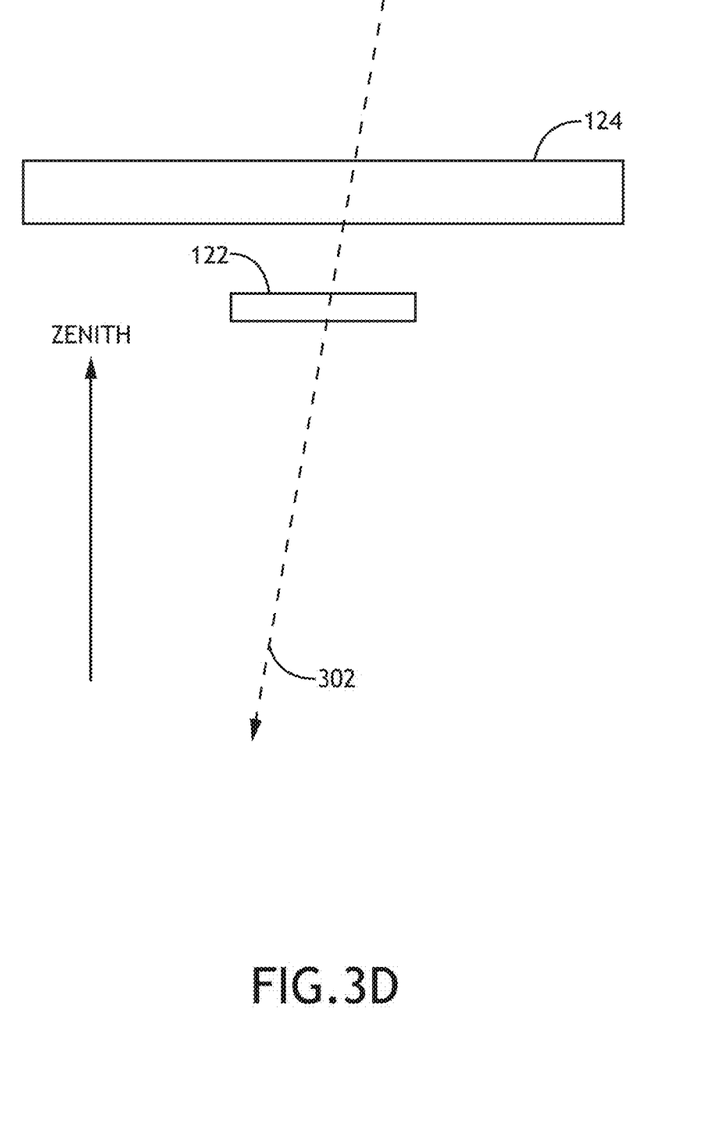
FIG. 3D is a schematic diagram illustrating the positioning of a single radiation sensor proximate to a horizontal illumination sensor, in accordance with one or more embodiments of the present disclosure.

FIGS. 3A through 3D are simplified schematic diagrams illustrating four non-limiting embodiments of the placement of one or more radiation sensors 124 relative to an illumination sensor 122. FIG. 3A illustrates the placement of a single radiation sensor 124 with an active area larger than the active area of the illumination sensor 122, in accordance with one or more embodiments of the present disclosure. The illumination sensor 122 is placed vertically to minimize the incidence of high-energy radiation from the zenith. FIG. 3B illustrates the placement of multiple radiation sensors 124 around the illumination sensor 122, in accordance with one or more embodiments of the present disclosure. FIG. 3C illustrates a curved radiation sensor 124 placed proximate to the illumination sensor 122, in accordance with one or more embodiments of the present disclosure. It is noted herein that the ability of one or more radiation sensors 124 to capture beams of radiation that pass through the illumination sensor 122 depends multiple factors including, but not limited to, the size of the radiation sensor 124 and the separation between radiation sensor 124 and the illumination sensor 122. For example, a beam of radiation described by path 302 passing through the illumination sensor 122 is captured by one or more radiation sensors 124 in the embodiments illustrated in FIGS. 3B and 3C, but not by the embodiment illustrated in FIG. 3A. It is noted that one or more radiation sensors 124 may be placed at any angle relative to the zenith. FIG. 3D is a simplified schematic diagram illustrating a horizontally-oriented illumination sensor 122 and a proximate horizontally-oriented radiation sensor 124 oriented, in accordance with one or more embodiments of the present disclosure.

In one embodiment, the system 100 includes a controller 126 communicatively coupled to an illumination sensor 122 and a proximate radiation sensor 124. In one embodiment, the controller 126 includes one or more processors 125. In another embodiment, the one or more processors 125 are configured to execute a set of program instructions maintained in a memory medium 127, or memory.

The one or more processors 125 of a controller 126 may include any processing element known in the art. In this sense, the one or more processors 125 may include any microprocessor-type device configured to execute algorithms and/or instructions. In one embodiment, the one or more processors 125 may consist of a desktop computer, mainframe computer system, workstation, image computer, parallel processor, or any other computer system (e.g., networked computer) configured to execute a program configured to operate the system 100, as described throughout the present disclosure. It is further recognized that the term "processor" may be broadly defined to encompass any device having one or more processing elements, which execute program instructions from a non-transitory memory medium 127. Therefore, the above description should not be interpreted as a limitation on the present invention but merely an illustration.

The memory medium 127 may include any storage medium known in the art suitable for storing program instructions executable by the associated one or more processors 125. By way of a non-limiting example, the memory medium 127 may include a non-transitory memory medium. By way of additional non-limiting examples, the memory medium 127 may include, but is not limited to, a read-only memory, a random access memory, a magnetic or optical memory device (e.g., disk), a magnetic tape, a solid state drive and the like. It is further noted that memory 127 may be housed in a common controller housing with the one or more processors 125. In an alternative embodiment, the memory 127 may be located remotely with respect to the physical location of the one or more processors 125 of controller 126. For instance, the one or more processors 125 of controller 126 may access a remote memory (e.g., server), accessible through a network (e.g., internet, intranet and the like).

In one embodiment, an illumination source 101 is configured to illuminate at least a portion of a sample 106 with a beam of illumination 102. In another embodiment, an illumination sensor 122 and one or more radiation sensors 124 are communicatively coupled to one or more controllers 126 such that the one or more controllers 126 are configured to receive an illumination signal from the illumination sensor 122 and a radiation signal from the one or more radiation sensors 124. In another embodiment, the one or more controllers 126 are configured to identify a set of illumination detection events based on the illumination signal. In another embodiment, the one or more controllers are configured to identify a set of radiation detection events based on the one or more radiation signals. In another embodiment, the one or more controllers 126 are configured to generate a set of coincidence events based on a comparison of the set of illumination detection events to the set of radiation detection events such that the set of coincidence events comprises simultaneous illumination detection events and radiation detection events. In another embodiment, one or more controllers 126 are configured to exclude the set of coincidence events from the set of illumination detection events in order to generate a set of identified features on the sample. It is noted herein that the set of identified features on the sample may include, but is not limited to, defect sites on the sample. In another embodiment, the memory 127 is configured to store the output of one or more of the various steps described herein.

The determination of the set of illumination detection events and/or the set of radiation detection events may be performed using any method known in the art including, but not limited to, a thresholding technique. By way of non-limiting example, the set of radiation detection events may be formed based on a thresholding technique in which a radiation detection event occurs upon the detection of radiation above a certain predetermined value. It is noted herein that the threshold of the radiation sensor 124 may be adjusted to optimize the ratio of false coincidence events to the false count rejection events, either of which may, but are not limited to, depend on sample type, sample quality, or the local radiation environment.

It is recognized herein that the steps described throughout the present disclosure may be carried out by a single controller 126 or, alternatively, multiple controllers 126. It is further noted herein that the one or more controllers 126 may be housed in a common housing or within multiple housings. In this way, any controller or combination of controllers may be separately packaged as a module suitable for integration into a complete inspection system 100. By way of a non-limiting example, a first controller may be configured to perform the step of identifying a set of illumination detection events based on an illumination signal received from the illumination sensor. One or more additional controllers may then be configured to perform the steps of: identifying a set of radiation detection events based on one or more radiation signals received from the one or more radiation sensors, comparing the set of radiation detection events to the set of illumination detection events to generate a set of coincidence events, and excluding the set of coincidence events from the set of illumination detection events to generate a set of identified features on the sample.

By way of a second non-limiting example, a first controller may be configured to perform the step of identifying a set of radiation detection events based on one or more radiation signals received from the one or more radiation sensors. One or more additional controllers may be configured to perform the steps of identifying a set of illumination detection events, comparing the set of radiation detection events to the set of illumination detection events to generate a set of coincidence events, and excluding the set of coincidence events from the set of illumination detection events to generate a set of identified features on the sample. In one embodiment, a first controller is configured to perform the step of identifying a set of radiation detection events based on one or more radiation signals received from the one or more radiation sensors. A second controller including one or more field programmable gate arrays (FPGAs) attached to an illumination sensor 122 is configured to perform the steps of identifying a set of illumination detection events, comparing the set of radiation detection events to the set of illumination detection events to generate a set of coincidence events, and excluding the set of coincidence events from the set of illumination detection events to generate a set of identified features on the sample. It is noted herein that one or more controllers including one or more FPGAs may be integrated into electronics associated with an illumination sensor 122 to perform pre-processing of an illumination signal. In this way, a set of radiation detection events may be an input into a pre-processing algorithm such that the output of the pre-processing algorithm is a set of identified features on the sample including corrections for radiation-induced false counts.

It is noted herein that timestamps may be associated with illumination detection events measured by an illumination sensor 122 and/or with radiation detection events measured by one or more radiation sensors 124 for the purpose of identifying false counts in an illumination sensor 122 generated by background radiation. In one embodiment, an illumination source 101 is configured to illuminate at least a portion of a sample 106 with a beam of illumination 102. In another embodiment, a controller 126 is communicatively coupled to a detector assembly 120 including an illumination sensor 122 and one or more radiation sensors 124. In another embodiment, a controller 126 is configured to identify a set of radiation detection events based on one or more radiation signals from one or more radiation sensors 124 and is further configured to generate a set of radiation timestamps associated with the set of radiation detection events. In another embodiment, a controller 126 is configured to identify a set of illumination detection events based on the illumination signal received from the illumination sensor 122 and is further configured to generate a set of illumination detection event timestamps associated with the set of imaging events. In another embodiment, a controller 126 is configured to compare the set of illumination detection event timestamps with the set of radiation detection event timestamps to generate a set of coincidence events based on the detection and radiation timestamps. In another embodiment, a controller 126 is configured to exclude the set of coincidence timestamps to generate a set of identified features on the sample 106 that are associated with identified defect sites on the sample 106.

It is noted herein that an illumination detection event by an illumination sensor 122 may be considered a false count if a proximate radiation sensor 124 detects a simultaneous radiation detection event. However, there will be a non-zero time difference between an illumination detection event by an illumination sensor 122 and a radiation detection event by a radiation sensor 124, which is related to the propagation time of the beam of radiation between the two sensors. Additionally, factors including, but not limited to, the clock speed of a controller 126, the readout speed of the illumination sensor 122, or the readout speed of a radiation sensor 124 may further limit the ability to detect the precise time difference between detection events. An illumination detection event by an illumination sensor 122 and a radiation detection event by a radiation sensor 124 may be, but is not limited to be considered simultaneous if the time difference between the two events is indistinguishable by the system 100. It is noted herein that the requirements for simultaneous detection are not intended to be limiting. For example, the time resolution associated with the detection of simultaneous events may be adjusted in order to adjust the sensitivity of the system 100. By way of a non-limiting example, a time resolution of tens of microseconds associated with the detection of simultaneous events may be sufficient to provide an acceptable false count mitigation rate.

Figure 4:
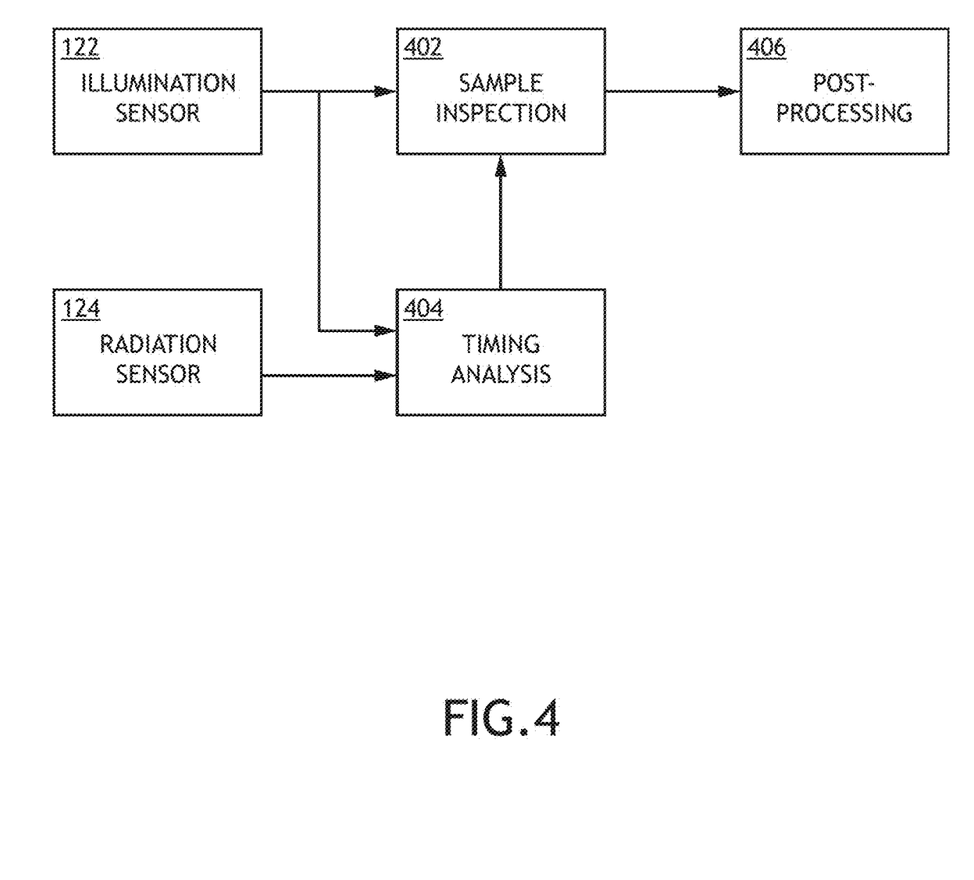
FIG. 4 is a simple flow diagram illustrating coupling between an illumination sensor, a radiation sensor, a sample inspection controller, a timing analysis controller, and a post-processing controller, in accordance with one or more embodiments of the present disclosure.

It is noted herein that the mitigation of radiation-induced false counts need not occur in real time by a system 100. FIG. 4 is a simple flow diagram illustrating coupling between an illumination sensor, a radiation sensor, a sample inspection controller, a timing analysis controller, and a post-processing controller, in accordance with one or more embodiments of the present disclosure. In one embodiment, an illumination sensor 122 is configured to detect illumination from a sample 106 and is further configured to transmit an illumination signal to a sample inspection controller 402 configured to inspect a sample 106. The sample inspection controller 402 may be configured to perform any type of sample inspection known in the art including, but not limited to, imaging or defect detection. In another embodiment, a timing analysis controller 404 is communicatively coupled to the illumination sensor 122 and one or more radiation sensors 124. In another embodiment, the timing analysis controller 404 is configured to receive one or more radiation signals from the one or more radiation sensors 124. In another embodiment, the timing analysis controller 404 is further configured to identify radiation detection events associated with the detection of radiation not associated with the sample 106 and to transmit timing information associated with the radiation detection events to post-processing controller 406. In another embodiment, the timing analysis controller 404 is further configured to receive a synchronization signal from the illumination sensor 122 in order to correlate radiation detection events with input from the illumination sensor. The synchronization signal may include, but is not limited to, illumination acquisition start and stop times. In one embodiment, a post-processing controller 406 correlates timing information associated with radiation detection events to outputs of the sample inspection controller 402 in order to remove false counts associated with radiation-induced events detected by the illumination sensor 122. In another embodiment, the timing controller 404 provides a list of radiation detection events to the post-processing controller 406 for binning. It is noted herein that the steps performed by controllers 402, 404, and 406 may be alternatively be carried out by a single controller 126 or by any combination of controllers. It is further noted that any controller or combination of controllers may be housed in a common housing or within multiple housings. In this way, the time-based radiation-induced false count mitigation sub-system may be modularized and packaged and integrated into an existing inspection system platform. Therefore, the above description should be interpreted as illustrative rather than limiting.

It is noted herein that the utilization of separate controllers associated with sample inspection controller 402, timing analysis controller 404 and post-processing controller 406 enables the modularization of the time-based radiation-induced false count mitigation system, which may facilitate integration with the hardware and/or software associated with existing wafer inspection systems. In this way, any inspection system known in the art may be improved by the addition of a radiation-induced false count mitigation system. It is further noted herein that additional reduction of radiation-induced false counts in an inspection system may be achieved by the incorporation of one or more radiation shields 118 by orienting the illumination sensor 122 vertically, and by reducing the pixel volume of the illumination sensor 122 as previously described herein.

It is noted herein that detector assemblies (e.g. 120) may experience false counts even with a radiation-induced false count mitigation system. In one embodiment, two or more detector assemblies 120 communicatively coupled to a controller 126 are used to further reduce radiation-induced false counts in an inspection system. In one embodiment, each detector assembly includes an illumination sensor 122. In another embodiment, each detector assembly includes one or more radiation sensors 124 proximate to an illumination sensor 122. A false count associated with one detector assembly is highly unlikely to occur in a second detector assembly. By utilizing multiple detector assemblies, the total number of false counts in a system 100 may be further reduced. In one embodiment, multiple detector assemblies are oriented to detect illumination scattered and/or reflected at multiple solid angles. It is noted herein that a metric or filter may be developed to capture known defect types while rejecting the number of false coincidence events based on expected illumination patterns at the multiple solid angles detected by the one or more detector assemblies 120.

Figure 5:
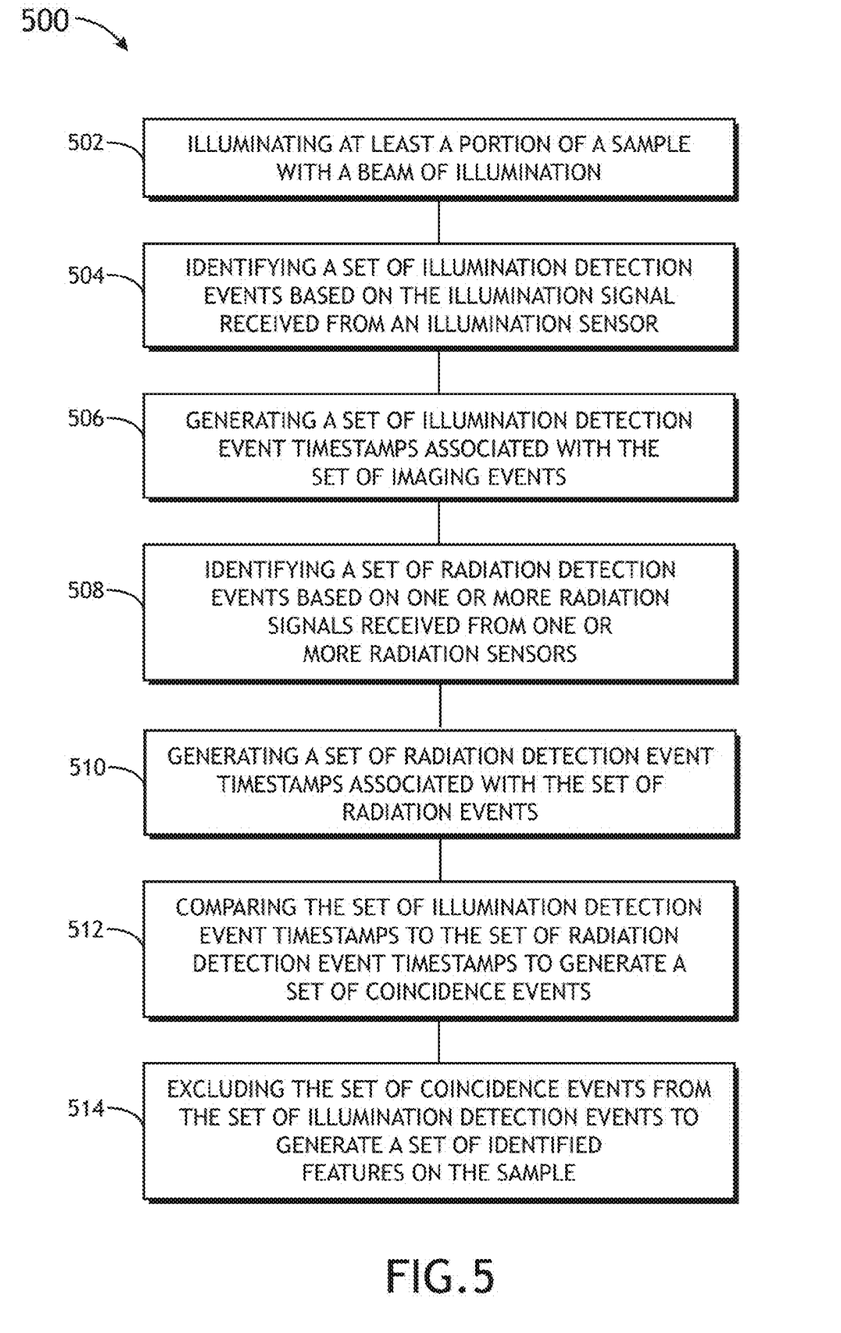
FIG. 5 is a flow diagram depicting a method for reducing radiation-induced false counts on a detector in an inspection system, in accordance with one or more embodiments of the present disclosure.

FIG. 5 illustrates a flow diagram illustrating a method for reducing radiation-induced false counts on a detector in an inspection system in accordance with one embodiment of the present disclosure. In one embodiment, the method includes the step 502 of illuminating at least a portion of a sample with a beam of illumination. In another embodiment, the method includes the step 504 of identifying a set of imaging events based on the illumination signal received from an illumination sensor. In another embodiment, the method includes the step 506 of generating a set of imaging event timestamps associated with the set of imaging events. In another embodiment, the method includes the step 508 of identifying a set of radiation detection events based on one or more radiation signals received from one or more radiation sensors. In another embodiment, the method includes the step 510 of generating a set of radiation detection event timestamps associated with the set of radiation detection events. In another embodiment, the method includes the step 512 of comparing the set of imaging event timestamps to the set of radiation detection event timestamps to generate a set of coincidence events. In this way, the set of coincidence events comprises illumination detection events and radiation detection events with matching timestamps. In another embodiment, the method includes the step 514 of excluding the set of coincidence events from the set of imaging events to generate a set of identified defect sites on the sample.

It is noted that the set of elements of system 100 as described above and illustrated in FIGS. 1 through 5 are provided merely for illustration and should not be interpreted as limiting. It is anticipated that a number of equivalent or additional configurations may be utilized within the scope of the present invention. By way of non-limiting example, additional elements including, but not limited to beam blocks or radiation shields 118 may be included in the system 100 in order to prevent unwanted signals that may generate false positives from reaching either the illumination sensor 122 or the one or more radiation sensors 124. For example, one or more radiation shields 118 with sufficient thermal and/or electrical properties may be directly bonded to a sensor package (e.g. a ceramic sensor package) to minimize space requirements and/or cost.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the disclosure is defined by the appended claims.

What is claimed is:

1. An inspection system with radiation-induced false count mitigation, comprising:
  an illumination source configured to illuminate a sample;
  a detector assembly comprising:
    an illumination sensor configured to detect illumination from the sample positioned on a first side of the illumination sensor; and
    one or more radiation sensors configured to detect particle radiation, wherein the one or more radiation sensors are positioned on a second side of the illumination sensor opposite of the first side of the illumination sensor; and
  one or more controllers communicatively coupled to the illumination sensor and the one or more radiation sensors, wherein the one or more controllers are configured to:
    identify a set of illumination detection events based on an illumination signal received from the illumination sensor;
    identify a set of radiation detection events based on one or more radiation signals received from the one or more radiation sensors;
    compare the set of radiation detection events to the set of illumination detection events to identify a set of coincidence events, wherein the set of coincidence events corresponds to simultaneous occurrences of radiation detection events and illumination detection events; and
    exclude the set of coincidence events from the set of illumination detection events to generate a set of identified features on the sample.

2. The system of claim 1, wherein the one or more controllers comprise:
  a first controller configured to identify a set of illumination detection events based on an illumination signal received from the illumination sensor, and
  one or more additional controllers configured to:
    identify a set of radiation detection events based on one or more radiation signals received from the one or more radiation sensors;
    compare the set of radiation detection events to the set of illumination detection events to identify a set of coincidence events, wherein the set of coincidence events corresponds to simultaneous occurrences of radiation detection events and illumination detection events; and
    exclude the set of coincidence events from the set of illumination detection events to generate a set of identified features on the sample.

3. The system of claim 1, further comprising:
  one or more additional detector assemblies communicatively coupled to the one or more controllers.

4. The system of claim 3, wherein the one or more controllers are further configured to:
  generate one or more additional sets of identified features on the sample based on one or more signals received from the one or more additional detector assemblies, and
  compare the set of identified features on the sample to the one or more additional sets of identified features on the sample to generate a modified set of identified features on the sample, wherein the modified set of identified features on the sample corresponds to features identified by at least two detector assemblies.

5. The system of claim 1, wherein the detector assembly includes one or more radiation shields positioned around one or more surfaces of the illumination sensor to block radiation from reaching the illumination sensor, wherein the one or more radiation shields are open on the first side of the illumination sensor to allow illumination from the sample to pass to the illumination sensor.

6. The system of claim 5, wherein the one or more radiation shields are formed from at least one of tungsten or lead.

7. The system of claim 5, wherein at least a portion of the one or more radiation shields is further configured as a heat sink.

8. The system of claim 1, wherein the one or more illumination sensors comprise:
at least one of one or more single-pixel sensors or one or more multi-pixel sensors.

9. The system of claim 8, wherein the one or more single-pixel sensors comprise:
at least one of one or more photomultiplier tubes (PMTs), one or more photodiodes, or one or more avalanche photodiode (APD) devices.

10. The system of claim 8, wherein the one or more multi-pixel sensors comprise:
at least one of one or more charge-coupled devices (CCDs), or one or more complementary metal-oxide semiconductor (CMOS) devices.

11. The system of claim 1, wherein the one or more first radiation sensors of a first detector are configured to have a larger active area than an active area of the illumination sensor of the first detector.

12. The system of claim 1, wherein the one or more illumination sensors are positioned vertically.

13. The system of claim 1, wherein the one or more radiation sensors are configured to detect at least one of muons, alpha particles, beta particles, or gamma radiation.

14. The system of claim 1, wherein the one or more radiation sensors include one or more scintillation sensors.

15. The system of claim 1, wherein the set of identified features on the sample includes one or more defect sites.

16. An inspection system with radiation-induced false count mitigation, comprising:
an illumination source configured to illuminate a sample;
a detector assembly comprising:
an illumination sensor configured to detect illumination from the sample positioned on a first side of the illumination sensor; and
one or more radiation sensors configured to detect particle radiation, wherein the one or more radiation sensors are positioned on a second side of the illumination sensor opposite of the first side of the illumination sensor; and
one or more controllers communicatively coupled to the illumination sensor and the one or more radiation sensors, wherein the one or more controllers are configured to:
identify a set of radiation detection events based on one or more radiation signals received from the one or more radiation sensors;
generate a set of radiation detection event timestamps associated with the set of radiation detection events;
identify a set of illumination detection events based on the illumination signal received from the illumination sensor;
generate a set of illumination detection event timestamps associated with the set of imaging events;
compare the set of illumination detection event timestamps to the set of radiation detection event timestamps to generate a set of coincidence events, wherein the set of coincidence events comprises illumination detection events and radiation detection events with matching timestamps; and
exclude the set of coincidence events from the set of illumination detection events to generate a set of identified features on the sample.

17. The system of claim 16, wherein the one or more controllers include a first controller and one or more additional controllers,
wherein the first controller is configured to:
identify a set of radiation detection events based on one or more radiation signals received from the one or more radiation sensors; and
generate a set of radiation detection event timestamps associated with the set of radiation detection events; and
wherein one or more additional controllers are configured to:
identify a set of illumination detection events based on the illumination signal received from the illumination sensor;
generate a set of illumination detection event timestamps associated with the set of imaging events;
compare the set of illumination detection event timestamps to the set of radiation detection event timestamps to generate a set of coincidence events, wherein the set of coincidence events comprises illumination detection events and radiation detection events with matching timestamps; and
exclude the set of coincidence events from the set of illumination detection events to generate a set of identified features on the sample.

18. The system of claim 16, wherein the one or more controllers are further configured to receive one or more synchronization signals from the illumination sensor, and wherein the set of radiation detection event timestamps is synchronized with the one or more synchronization signals.

19. The system of claim 16, further comprising:
one or more additional detector assemblies communicatively coupled to the one or more controllers.

20. The system of claim 19, wherein the one or more controllers are further configured to:
generate one or more additional sets of identified features on the sample based on one or more signals received from the one or more additional detector assemblies; and
compare the set of identified features on the sample to the one or more additional sets of identified features on the sample to generate a modified set of identified features on the sample, wherein the modified set of identified features on the sample corresponds to features identified by at least two detector assemblies.

21. The system of claim 16, wherein the detector assembly includes one or more radiation shields positioned to block radiation from reaching the illumination sensor.

22. The system of claim 21, wherein the one or more radiation shields is comprised of at least one of tungsten or lead.

23. The system of claim 21, wherein at least a portion of the one or more radiation shields is further configured as a heat sink.

24. The system of claim 16, wherein the one or more illumination sensors comprise at least one of one or more single-pixel sensors or one or more multi-pixel sensors.

25. The system of claim 24, wherein the one or more single-pixel sensors comprise at least one of photomultiplier tubes (PMTs) or photodiodes.

26. The system of claim 24, wherein the one or more multi-pixel sensors comprise at least one of charge-coupled devices (CCDs) or complementary metal-oxide semiconductor (CMOS) devices.

27. The system of claim 16, wherein the one or more first radiation sensors of a first detector are configured to have a larger active area than an active area of the illumination sensor of the first detector.

28. The system of claim 16, wherein the one or more illumination sensors are positioned vertically.

29. The system of claim 16, wherein the one or more radiation sensors are configured to detect at least one of muons, alpha particles, beta particles, or gamma radiation.

30. The system of claim 16, wherein the one or more radiation sensors comprise one or more scintillation sensors.

31. The system of claim 16, wherein the set of identified features on the sample includes one or more defect sites.

32. A method for reducing radiation-induced false counts on a detector in an inspection system, comprising illuminating at least a portion of a sample with a beam of illumination;

identifying, with an illumination sensor, a set of illumination detection events based on the illumination signal received from an illumination, wherein the sample is positioned on a first side of the illumination sensor;

generating a set of illumination detection event timestamps associated with the set of imaging events;

identifying a set of radiation detection events based on one or more radiation signals received from one or more radiation sensors;

generating, with one or more radiation sensors positioned on a second side of the illumination sensor opposite of the first side of the illumination sensor, a set of radiation detection event timestamps associated with the set of radiation detection events;

comparing the set of illumination detection event timestamps to the set of radiation detection event timestamps to generate a set of coincidence events, wherein the set of coincidence events comprises illumination detection events and radiation detection events with matching timestamps; and excluding the set of coincidence events from the set of illumination detection events to generate a set of identified defect sites on the sample.

\* \* \* \* \*